United States Patent
Grinnell et al.

(10) Patent No.: US 8,076,298 B2
(45) Date of Patent: Dec. 13, 2011

(54) TREATING ACUTE RENAL FAILURE WITH SOLUBLE THROMBOMODULIN VARIANTS

(75) Inventors: Brian William Grinnell, Indianapolis, IN (US); Bryan Edward Jones, Carmel, IN (US); Bruce A. Molitoris, Indianapolis, IN (US)

(73) Assignees: Eli Lilly and Company, Indianapolis, IN (US); Indiana University Research and Technology Corporation, Indianapolis, IN (US)

( * ) Notice: Subject to any disclaimer, the term of this patent is extended or adjusted under 35 U.S.C. 154(b) by 161 days.

(21) Appl. No.: 12/514,812

(22) PCT Filed: Dec. 10, 2007

(86) PCT No.: PCT/US2007/086965
§ 371 (c)(1),
(2), (4) Date: May 14, 2009

(87) PCT Pub. No.: WO2008/073884
PCT Pub. Date: Jun. 19, 2008

(65) Prior Publication Data
US 2010/0087368 A1    Apr. 8, 2010

Related U.S. Application Data

(60) Provisional application No. 60/869,565, filed on Dec. 12, 2006.

(51) Int. Cl.
*A01K 38/00* (2006.01)
(52) U.S. Cl. ...................................................... 514/21.2
(58) Field of Classification Search ................. 514/21.2
See application file for complete search history.

(56) References Cited

FOREIGN PATENT DOCUMENTS

| EP | 0 412 841 A1 | 2/1991 |
| WO | WO 2007/047430 | 4/2007 |

OTHER PUBLICATIONS

Faioni, Elena M. et al., "Mutations in the thrombomodulin gene are rare in patients with severe thrombophilia", *British Journal of Haematology*, Aug. 2, 2002, pp. 595-599, vol. 118.
Database Uniprot, ebi; Nov. 28, 2006,"TRBM_HUMAN—entry version 105" XP002503077 retrieved from EBI accession No., UNIPROT:P07204 Database accession No. P07204.
Parkinson, J.F., et al., "Stable Expression 1-6, 9, 12 of a Secretable Deletion Mutant of Recombinant Human Thrombomodulin in Mammalian Cells", Journal of Biological Chemistry, vol. 265, No. 21, 1990, pp. 12602-12610.

*Primary Examiner* — Maryam Monshipouri
(74) *Attorney, Agent, or Firm* — Alejandro Martinez

(57) ABSTRACT

The present invention provides a method for preventing and/or treating subjects with acute renal failure caused by a variety of conditions. The method comprises administering to the subject soluble thrombomodulin which does not activate Protein C. In conjunction with standard of care, soluble thrombomodulin that does not activate Protein C will prevent or reduce acute kidney injury and subsequent morbidity and mortality.

4 Claims, No Drawings

TREATING ACUTE RENAL FAILURE WITH SOLUBLE THROMBOMODULIN VARIANTS

This U.S. national phase application of PCT/US2007/086965, filed Dec. 10, 2007, claims priority to U.S. provisional patent application Ser. No. 60/869,565, filed Dec. 12, 2006.

FIELD OF THE INVENTION

This invention relates to medical science particularly the prevention and treatment of acute renal failure with soluble thrombomodulin.

BACKGROUND OF THE INVENTION

Acute renal failure (ARF) is a general term referring to conditions resulting from an acute insult to the microvasculature of the kidney. Although the exact nature of the acute insult may vary, ARF is generally characterized by a sudden decline in glomerular filtration rate, the accumulation of nitrogen wastes and the inability of the kidney to regulate electrolyte and water balance.

Despite the technical advances in the care of patients who suffer from ARF and improvements in the understanding of the pathophysiology of the disease progress, there is still a high mortality associated with this condition. This is especially true in the ICU setting where ARF is associated with a mortality of 50-90%. Although numerous experimental models have shown that a variety of agents, including dopamine, osmotic agents, atrial natriuretic peptide, insulin like growth factor and endothelial receptor antagonists are effective in animal models, these agents have been ineffective in clinical studies of ARF.

Thrombomodulin (TM) is a glycoprotein anchored on the membrane surface of endothelial cells on many organs, including lung, liver, and kidney and has been shown to possess well established roles in inflammation, fibrinolysis, apoptosis, cell adhesion and cellular proliferation. TM can complex with thrombin to inhibit thrombin's pro-coagulant activity and once complexed, the TM/thrombin complex can enhance the activation of Protein C (PC) 1000 fold. Activated PC (APC) also modulates the coagulation cascade in addition to possessing anti-inflammatory properties.

TM is composed of five domains: an N-terminal lectin-like binding domain, an epidermal growth factor (EGF) domain which consists of 6 EGF-like repeats, a Ser/Thr-rich region, a transmembrane domain and a cytoplasmic domain. Soluble TM variants have been constructed by deleting the cytoplasmic and transmembrane domains. To attempt to understand TM function, additional TM variants have been generated. TM deletion variants have been used to determine the smallest TM fragment (EGF-like repeats 4-6) which retains thrombin binding and PC activation. Nagashima and colleagues used alanine scanning of this TM region to determine residues which are critical for thrombomodulin activity. Changes of specific residues to alanine within polypeptides consisting of EGF 4-6 resulted in sTM variants with greatly reduced levels of PC activation. However, the use of sTM or any sTM variant in the treatment of acute renal failure was not disclosed. (Nagashima et al, Journal of Biological Chemistry, 268(4): 2888-2892, 1993).

Recent results indicate that APC is effective in preventing ischemia/reperfusion induced renal injury in rats. (Mizutani et al., Blood, 95(12): 3781-3787, 2000). The study indicates that APC may prevent this renal injury by inhibiting leukocyte activation as well as by attenuating coagulation. Although the use of APC appears promising, the risks of inducing an anti-coagulation environment in an acute renal context are not known.

There remains a need for an alternative option for the treatment of acute renal failure that is both safe and effective. Accordingly, Applicants have discovered that soluble thrombomodulin variants, that do not activate Protein C, are unexpectedly effective in in vivo experimental models of ARF. Thus, using a soluble thrombomodulin variant which may not modulate the coagulation cascade offers a potentially significant alternative approach to the prevention and treatment of ARF.

SUMMARY OF THE INVENTION

The present invention provides soluble thrombomodulin (sTM) variants which do not activate Protein C. In a preferred embodiment, the sTM variant has the sequence of SEQ ID NO: 4.

The present invention provides a method of treating acute renal failure which comprises administering an effective amount of a sTM variant to a patient in need thereof, wherein the sTM variant does not activate Protein C. In a preferred embodiment, the present invention provides a method of treating acute renal failure which comprises administering an effective amount of a sTM variant to a patient in need thereof, wherein the sTM variant has a polypeptide sequence of SEQ ID NO:4.

In another embodiment, the present invention provides a method of preventing acute renal failure by administering an effective amount of a sTM variant to a patient in need thereof, wherein the sTM molecule does not activate Protein C. The present invention also provides a method of preventing acute renal failure which comprises administering an effective amount of a sTM variant, which does not activate Protein C, to a patient in need thereof, wherein said sTM variant has a sequence of SEQ ID NO: 4.

In still another embodiment, the present invention provides the use of a sTM variant which does not activate PC for treating acute renal failure in a patient. In a more preferred embodiment, the present invention provides the use of a sTM variant, which does not activate Protein C for treating acute renal failure in a patient, wherein the sTM has a sequence of SEQ ID NO: 4. In another embodiment, the present invention provides the use of a sTM variant which does not activate PC for the manufacture of a medicament for treating acute renal failure in a patient. In a more preferred embodiment, the present invention provides the use of a sTM variant, which does not activate Protein C for the manufacture of a medicament for treating acute renal failure in a patient, wherein the sTM has a sequence of SEQ ID NO: 4.

The present invention also provides the use of a sTM variant which does not activate PC for preventing acute renal failure in a patient. In a more preferred embodiment, the present invention provides the use of a sTM variant, which does not activate Protein C for preventing acute renal failure in a patient, wherein the sTM has a sequence of SEQ ID NO: 4. The present invention also provides the use of a sTM variant which does not activate PC for the manufacture of a medicament for preventing acute renal failure in a patient. In a more preferred embodiment, the present invention provides the use of a sTM variant, which does not activate Protein C for the manufacture of a medicament for preventing acute renal failure in a patient, wherein the sTM has a sequence of SEQ ID NO: 4.

The present invention also provides for a pharmaceutical composition comprising a sTM variant of SEQ ID NO: 4.

DETAILED DESCRIPTION OF THE INVENTION

Definitions

For purposes of the present invention, as disclosed and claimed herein, the following terms are as defined below.

"ARF"—refers to acute renal failure which has as one symptom an acute reduction in glomerular filtration rate associated with the retention of nitrogenous wastes. The reduction may be due to an acute kidney injury such as acute tubular necrosis or acute interstitial nephritis. Acute renal failure alternatively may be referred to as acute renal dysfunction.

"sTM"—refers to soluble thrombomodulin of SEQ ID NO:3.

"sTM variant"—refers to a sTM with one or more substitutions when compared to SEQ ID NO: 3.

"Effective amount"—a therapeutically efficacious amount of a sTM variant. The particular dose of the sTM variant administered according to this invention will, of course, be determined by the attending physician evaluating the particular circumstances surrounding the case, including the compound administered, the particular condition being treated, the patient characteristics and similar considerations.

"Treating" or "treat"—describes the management and care of a patient to eliminate, reduce, or control a disease, condition, or disorder.

"Preventing" or "prevent"—describes the management and care of a patient to delay onset of the symptoms or complications of a disease, condition, or disorder Soluble thrombomodulin (sTM), is a soluble, secreted variant of thrombomodulin which lacks the full-length thrombomodulin transmembrane and cytoplasmic domains. The primary amino acid structure of human thrombomodulin (SEQ ID NO: 1) is known in the art, as described in EP 0412841 A1. Human TM is synthesized as a 575 amino acid protein including a signal peptide portion reported to be 16, 18, or 21 residues in length. Following the signal peptide portion, human TM comprises the following domains or regions, sequentially from the amino terminus: 1) an amino terminal domain of ~222-226 amino acids, 2) six EGF ("epidermal growth factor")-like structures of ~236-240 amino acids (EGF domain), 3) a serine/threonine rich domain (ST domain) of ~34-37 amino acids and having several possible O-glycosylation sites, 4) a transmembrane region of ~23-24 amino acids, and 5) a cytoplasmic domain of ~36-38 amino acids. As used herein, "amino terminal domain," "EGF domain," "ST domain," "transmembrane region' or domain," and "cytoplasmic region' or domain" refer to the approximate range of amino acid residues noted above for each region or domain. Further, because in vivo processing will be expected to vary depending upon the expressing transformed host cell, especially a prokaryotic host cell compared to a eukaryotic host cell, the term "amino terminal region' or domain" optionally may include the thrombomodulin signal peptide or portion thereof.

One of ordinary skill in the art will recognize that variations in the cleavage of the signal peptide will generate different sized proteins and will result in different numbering for amino acid positions. For illustrative purposes, amino acid position numbering will be based on SEQ ID NO: 3. The first alanine of SEQ ID NO:3 will be designated position 1 for numbering of amino acids.

Further, the sTM variants of the present invention are named as follows: one letter code for the substituted amino acid, the amino acid position number, followed by the replacing amino acid residue. For example, sTM Y376, designates tyrosine at position 376. Further Y376E, refers to a sTM variant in which the tyrosine at position 376 has been changed to a glutamic acid.

The sTM variants of the present invention do not activate Protein C. In a preferred embodiment, the sTM variant has a sequence of SEQ ID NO: 4:

```
Ala Pro Ala Glu Pro Gln Pro Gly Gly Ser Gln Cys Val Glu His Glu
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
            115                 120                 125

Val Pro Ser Glu Pro Ile Trp Glu Glu Gln Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175
```

-continued

```
Thr Pro Phe Ala Ala Arg Gly Ala Asp Phe Gln Ala Leu Pro Val Gly
            180                 185                 190
Ser Ser Ala Ala Val Ala Pro Leu Gly Leu Gln Leu Met Cys Thr Ala
            195                 200             205
Pro Pro Gly Ala Val Gln Gly His Trp Ala Arg Glu Ala Pro Gly Ala
            210                 215                 220
Trp Asp Cys Ser Val Glu Asn Gly Gly Cys Glu His Ala Cys Asn Ala
225                 230                 235                 240
Ile Pro Gly Ala Pro Arg Cys Gln Cys Pro Ala Gly Ala Ala Leu Gln
            245                 250                 255
Ala Asp Gly Arg Ser Cys Thr Ala Ser Ala Thr Gln Ser Cys Asn Asp
            260                 265                 270
Leu Cys Glu His Phe Cys Val Pro Asn Pro Asp Gln Pro Gly Ser Tyr
            275                 280                 285
Ser Cys Met Cys Glu Thr Gly Tyr Arg Leu Ala Ala Asp Gln His Arg
            290                 295                 300
Cys Glu Asp Val Asp Asp Cys Ile Leu Glu Pro Ser Pro Cys Pro Gln
305                 310                 315                 320
Arg Cys Val Asn Thr Gln Gly Gly Phe Glu Cys His Cys Tyr Pro Asn
            325                 330                 335
Tyr Asp Leu Val Asp Gly Glu Cys Val Glu Pro Val Asp Pro Cys Phe
            340                 345                 350
Arg Ala Asn Cys Glu Xaa358 Gln Cys Gln Pro Leu Asn Gln Thr Ser Tyr
            355                 360                 365
Leu Cys Val Cys Ala Glu Gly Xaa376 Ala Pro Ile Pro His Glu Pro His
            370                 375                 380
Arg Cys Gln Met Phe Cys Asn Gln Thr Ala Cys Pro Ala Asp Cys Asp
385                 390                 395                 400
Pro Asn Thr Gln Ala Ser Cys Glu Cys Xaa410 Glu Gly Tyr Ile Leu Asp
                405                 410                 415
Asp Gly Phe Ile Cys Thr Asp Ile Asp Glu Cys Glu Asn Gly Gly Phe
            420                 425                 430
Cys Ser Gly Val Cys His Asn Leu Pro Gly Thr Phe Glu Cys Ile Cys
            435                 440                 445
Gly Pro Asp Ser Ala Leu Ala Arg His Ile Gly Thr Asp Cys Asp Ser
            450                 455                 460
Gly Lys
465
``` wherein

Xaa at position 358 is Tyr, Asp, Glu, Asn, or Gln,

Xaa at position 376 is Phe, Gly, Ile, Leu, or Val, or

Xaa at position 410 is Pro or Leu. (SEQ ID NO: 4).

In a more preferred embodiment, the present invention provides a soluble thrombomodulin variant having a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13. In a more preferred embodiment, the present invention provides a soluble thrombomodulin variant having a sequence selected from the group consisting of SEQ ID NO: 6, SEQ ID NO: 9, SEQ ID NO: 10, and SEQ ID NO: 13. Preferred embodiments of the present invention are sTM variants having substitutions at amino acid positions 358, 376, or 410. In a preferred embodiment, the sTM variant has the sequence selected from the group consisting of Y358D (SEQ ID NO: 5), Y358E (SEQ ID NO: 6), Y358N (SEQ ID NO: 7), and Y358Q (SEQ ID NO: 8). In a more preferred embodiment, the sTM variant has the sequence Y358E. In another embodiment, a sTM variant has a sequence selected from the group consisting of F376I (SEQ ID NO: 9), F376L (SEQ ID NO: 10), F376V (SEQ ID NO: 11), and F376G (SEQ ID NO: 12). In a more preferred embodiment, the sTM variant has a sequence selected from the group consisting of F376I and F376L. In a even more preferred embodiment, the sTM variant has a sequence F376L. In a preferred embodiment, the sTM variant has the sequence F367I. Another embodiment of the present invention is a sTM variant having an amino acid substitution of proline at position 410. In a more preferred embodiment, the sTM variant has the sequence P410L (SEQ ID NO: 13).

Methods to produce human recombinant soluble thrombomodulin have been described previously (Parkinson et al., 1990 J. Biol. Chem. 265: 12602-12610). This invention embraces molecular genetic manipulations that can be achieved in a variety of ways known in the art. The recombinant cells, plasmids, and DNA sequences of the present invention provide a means to produce pharmaceutically useful compounds wherein the compound, secreted from recombinant cells, is a soluble thrombomodulin variant.

Generally, the definitions of nomenclature and descriptions of general laboratory procedures used in this application can be found in J. Sambrook et al., *Molecular Cloning, A Laboratory Manual*, (1989) Cold Spring Harbor Laboratory, Cold Spring Harbor, N.Y. The manual is hereinafter referred to as Sambrook. In addition, Ausubel et al., eds., *Current Protocols in Molecular Biology*, (1987 and periodic updates) Greene Publishing Associates, Wiley-Interscience, New York, discloses methods useful in the present application.

Embodiments of this invention often involve the creation of novel sTM variants and genes encoding sTM variant by in vitro mutagenesis. Created genes are isolated in intermediate vectors and cloned for amplification in prokaryotes such as *E. coli*. *E. coli* is preferred because that organism is easy to culture and more fully understood than other species of prokaryotes. The Sambrook manual contains methodology sufficient to conduct all subsequently described clonings in *E. coli*. Representative vectors include pBR322 and the pUC series which are available from commercial sources.

sTM variants are generated by altering the amino acid sequence of human sTM (SEQ ID NO:3). Methods by which amino acids can be removed or replaced in the sequence of a protein are well known. See, e.g., Sambrook et al., supra; Ausubel et al., supra; U.S. Pat. No. 4,737,462; U.S. Pat. No. 4,588,585; EP-0285 123; and references cited therein. Genes that encode a peptide with an altered amino acid sequence can be made synthetically, for example. A preferred method is the use of site-directed in vitro mutagenesis. Sequential rounds of site-directed mutagenesis can be used to produce analogs with multiple substitutions.

It is expected that those of skill in the art are knowledgeable in the expression systems chosen for expression of the desired sTM variants. Briefly, the polynucleotides are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers, e.g., tetracycline, neomycin, and dihydrofolate reductase, to permit detection of those cells transformed with the desired DNA sequences. The vectors containing the polynucleotide sequences of interest (e.g., soluble thrombomodulin variant encoding sequences and expression control sequences) are transferred into the host cell by well-known methods, which vary depending on the type of cellular host. For example, calcium chloride transfection is commonly utilized for prokaryotic cells, whereas calcium phosphate treatment or electroporation may be used for other cellular hosts.

*E. coli* is a prokaryotic host useful particularly for cloning the polynucleotides of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Eukaryotic cells may also be used to express and produce the sTM variants of the present invention. For example, yeast, may be used for expression. *Pichia pastoris* is a preferred host, with suitable vectors having expression control sequences, such as promoters, including 3-phosphoglycerate kinase or other glycolytic enzymes, and an origin of replication, termination sequences and the like as desired. Additionally, mammalian tissue cell culture may also be used to express and produce the polypeptides of the present invention. Mammalian tissue culture is actually preferred, because a number of suitable host cell lines capable of secreting intact recombinant proteins have been developed in the art, and include the CHO cell lines, various COS cell lines, HeLa cells, myeloma cell lines, transformed B-cells, human embryonic kidney cell lines, or hybridomas. Preferred cell lines are CHO and myeloma cell lines such as SP2/0 and NS0.

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters such as SV40, adenovirus, bovine papilloma virus, cytomegalovirus and the like. Preferred polyadenylation sites include sequences derived from SV40 and bovine growth hormone.

Methods to determine the ability of human thrombomodulin to activate Protein C are known in the art. For example, a cell culture based assay as described in Grinnell and Berg. 1996. Am. J. Physiol. 270: H603-609 can be used to determine Protein C activation. In addition, this assay may be used to determine whether human sTM can activate rat PC in the presence of different factors. Briefly, human aortic endothelial cells, which provide endogenous TM, are incubated with combinations of human or rat protein C and human or rat thrombin and the amount of Protein C activation is measured by the rate of cleavage of a chromogenic substrate. The results are reported by establishing the rate obtained in the reaction with human thrombin and human Protein C as 100% PC activation and comparing the rates obtained under other conditions to this 100%. In this assay, endogenous human TM is unable to activate rat Protein C in the presence of rat thrombin (0% activation) and is deficient in activating rat Protein C in the presence of human thrombin (12.83%).

Grinnell and Berg, mentioned above, also describe a non-cell based assay to measure Protein C activation. Briefly, rat sTM, human sTM or a sTM variant are combined with rat Protein C and rat thrombin. sTM ability to activate rat Protein C is measured by the rate of Protein C dependent cleavage of a chromogenic substrate. As demonstrated in Example 1, rat thrombin and rat sTM activate rat PC. However, rat PC activation is more than ten fold reduced in the presence of human sTM and is not activated to any detectable degree by the sTM variant Y358L.

The present invention provides for the treatment and prevention of acute renal failure comprising administration of sTM variants that do not activate PC. The present invention provides a method of treating or preventing acute renal failure comprising administration of an effective amount of an sTM variant, which does not activate Protein C. In a preferred embodiment of the methods of the present invention, the sTM variant has the sequence SEQ ID NO: 4. In a more preferred embodiment of the methods of the present invention, the sTM variant is selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13. In a more preferred embodiment of the methods of the present invention, the sTM variant is selected from the group consisting of SEQ ID NO: 6, SEQ ID NO: 9, SEQ ID NO: 10, and SEQ ID NO: 13.

In another embodiment, the present invention provides the use of sTM variants, which do not activate Protein C, for therapy. In a preferred embodiment, the sTM variants, which do not activate Protein C, are used in the manufacture of a medicament for treating acute renal failure. In another preferred embodiment, the present invention provides the use of a sTM variant, which does not activate Protein C, for the manufacture of a medicament for preventing acute renal failure. In a preferred embodiment, the sTM variant, has a sequence of SEQ ID NO: 4. In another preferred embodiment, the sTM is selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13. In a more preferred embodiment, the sTM variant is selected from the group consisting of SEQ ID NO: 6, SEQ ID NO: 9, SEQ ID NO: 10, and SEQ ID NO: 13.

In vivo models of acute renal failure have been described. For example, Example 2 describes a LPS-induced acute renal failure rat model known by those of ordinary skill in the art. Kikeri et al., (1986) *Am. J. Physiol.* 250:F1098-F1106. The LPS-induced model generally consists of inducing acute renal failure with a bolus injection of *E. coli* LPS. The bolus injection of LPS causes endotoxemia, resulting in a decrease in GRF and an increase in blood-urea-nitrogen (BUN) levels. sTM variants may be tested for their ability to reduce or prevent this acute kidney injury by treating the rats with human sTM variants prior to induction of endotoxemia. Briefly, human or rat sTM is administered 12 hours prior to induction of endotoxemia by intraperitoneal administration of LPS, whereas control rats receive vehicle 12 hours prior to induction. Twenty-four hours after LPS or vehicle administration, the animals are sacrificed and blood samples are collected for blood-urea-nitrogen analysis. As shown in Example 2, administration of human or rat sTM, is able to reduce acute kidney injury as measured by reduction in BUN levels.

Further, the sTM variants of the present invention may also be tested in an ischemic rat model of ARF as in Example 3. Briefly, a sTM or a sTM variant is administered 24 hours prior to induction of renal ischemia. Renal ischemia is induced by a partial clamp of the abdominal aorta just below the renal arteries resulting in a decrease in blood flow by 90%. The clamp is maintained for one hour and then removed. Acute renal injury is then measured as an increase in serum creatinine levels. As shown in Table 3, administration of human sTM or a sTM variant significantly reduced the levels of serum creatinine compared to saline treated rats.

In a preferred embodiment, the sTM variants of the present invention are formulated in accordance with routine procedures as pharmaceutical compositions adapted for various modes of administration to human beings. The sTM variants of the present invention can be in the form of a composition comprising a sTM variant of the invention suspended in a pharmacologically acceptable diluent or excipient. These pharmaceutical compositions may be administered by any means known in the art that achieve the generally intended purpose to treat acute renal failure. The preferred route of administration is parenteral, defined herein as referring to modes of administration that include intravenous, intramuscular, intraperitoneal, intrasternal, subcutaneous, and intraarticular injection and infusion. More preferably, sTM variants will be administered either by IV bolus and/or subcutaneous injection. Preferred exposure times range from one to 24 or more hours, including but not limited to 48, 72, 96, or as many as 120 hours. The dosage administered will be dependent upon the age, health, and weight of the recipient, kind of concurrent treatment, if any, frequency of treatment, and the nature of the effect desired.

Compositions within the scope of the invention include all compositions wherein the sTM variant is present in an amount that is effective to achieve the desired medical effect for treating acute renal failure. The pharmaceutical compositions for administration are designed to be appropriate for the selected mode of administration, and pharmaceutically acceptable excipients such as, buffers, surfactants, preservatives, solubilizing agents, isotonicity agents, stabilizing agents, carriers, and the like are used as appropriate. *Remington's Pharmaceutical Sciences*, Mack Publishing Co., Easton Pa., latest edition, incorporated herein by reference, provides a compendium of formulation techniques as are generally known to practitioners.

The concentration of the sTM variant in formulations may be from as low as about 0.1% to as much as 15% or 20% by weight and will be selected primarily based on fluid volumes, viscosities, stability, and so forth, in accordance with the particular mode of administration selected. Preferred concentrations of the sTM variant will generally be in the range of 1 to about 100 mg/mL.

Typical dosage levels can be optimized using standard clinical techniques and will be dependent on the mode of administration and the condition of the patient. Generally, doses will be in the range of 1 µg/kg to 10 mg/kg.

The following examples are intended to illustrate but not to limit the invention.

Example 1

Rat Protein C Activation by sTM Variants

A kinetic analysis is done to determine the rate of activation of rat PC by various human sTM variants. For each sTM variant, the reactions are set up as follows. In a final 100 µL, reaction volume, rat Protein C is added to a final concentration of 150 nM and rat thrombin is added to a final concentration of 2 nM. STM or sTM variant in AB/BSA buffer (150 mM NaCl; 20 mM Tris pH 7.5; 3 mM $CaCl_2$; 1 mg/ml BSA) is added to the reaction at final concentrations varying from 0.5 nM to 30 nM. The reaction mixture is incubated 30 minutes at 37° C. 25 µL of each reaction is removed to a 96 well plate containing 150 µL of Thrombin Stop Buffer (1 unit/ml hirudin in 150 mM NaCl; 20 mM Tris pH 7.5; 3 mM $CaCl_2$) and incubated 5 minutes at room temperature. 25 µL, of a 4 µM stock solution of S2366 chromogenic substrate (L-Pyroglutamyl-L-prolyl-L-arginine-p-Nitroaniline hydrochloride, Chromogenix) is added and mixed briefly. The Optical Density at 405 nm (OD405) is read on a microplate spectrophotometer (Molecular Devices SPECTRAmax) in a five minute kinetic read with a 6 second read interval. Michaelis Menton kinetic constants were calculated from the kinetic data using SigmaPlot software with the Enzyme Kinetics Module 1.1. "TLD" indicates too low for detection.

As shown in the results of a kinetic assay, human sTM (SEQ ID NO: 3) is able to activate rat PC, however the rate was more than 10 fold lower than that obtained by rat sTM (SEQ ID NO: 14). The rate of rat PC activation obtained with the sTM variant (SEQ ID NO: 10) tested was too low to detect, indicating that the sTM variant was unable to activate rat PC.

TABLE 1

| sTM variant | Vmax(mOD405/min) |
|---|---|
| Rat sTM | 47.1 |
| Human sTM | 3.1 |
| F376L | TLD |

Example 2

Efficacy of Human and Rat sTM in LPS-Induced Acute Renal Failure in Rats

Male Sprague-Dawley rats (Harlan, Ind., USA) weighing 200-250 g are used in the study. The animals are randomized into two groups at the time of surgery: 1) sham-treated and 2) LPS-treated animals. The animals in the LPS-treated group are further divided into subgroups vehicle, human sTM (hsTM-SEQ ID NO: 3), or rat sTM (rsTM—SEQ ID NO: 14). Endotoxemia is induced by intraperitoneal administration of E. coli LPS (20 mg/kg; Lipopolysaccharide W E. coli O111:B4, Sigma, Detroit, Mich.). The control group receives pyrogen-free saline. HsTM (2.5 mg/kg) or rsTM (2.5 mg/kg) is administered subcutaneously 12-h prior to the induction of endotoxemia. Animals are sacrificed 24-h post-LPS administration and blood samples are collected for BUN analysis. The results below are the average of 4 rats per group.

Human sTM and rat sTM are able to reduce BUN levels at comparable levels. The reduction of BUN levels by human sTM, even though human sTM is severely deficient in its ability to activate rat PC, indicates the reduction in the LPS-induced acute renal injury is not dependent on activation of PC.

TABLE 2

| Group | BUN (mg/dl) |
|---|---|
| Control | 20.4 |
| LPS | 76.35 |
| LPS + rat sTM | 38.55 |
| LPS + human sTM | 39.15 |

Example 3

Efficacy of sTM Variant in a Rodent Partial Aortic Clamp (PAC) Model

To evaluate the effect of pretreatment with a sTM variant on ischemic ARF, rats (200-250 g, Harlan Laboratories, Indianapolis, Ind.) are divided into two groups. STM (5 mg/kg) is administered subcutaneously to one group (treated) 24 hours prior to surgery, while an equal volume of saline is administered to the other group (untreated)) 24 hours prior to surgery. The night before surgery, rats are denied access to food but have access to water. Anesthesia is induced with 5% halothane and maintained with 1-1.5% halothane in oxygen enriched air via a face mask. After shaving the abdomen of the rat, a midline incision is made through the skin and musculature to expose the abdominal cavity. The abdominal aorta just below the renal arteries is then isolated through blunt dissection from the inferior vena cava, and an ultrasonic probe (2.0 mm diameter, Transit Time Perivascular Flowmeter TS420 (Transonic Systems, Inc, Ithica, N.Y.) placed and secured to quantify the infrarenal aortic blood flow rate. The upper abdominal aorta is then isolated through blunt dissection and freed from the surrounding structures to expose the aorta between the celiac artery and superior mesenteric artery.

The aortic clamp itself is comprised of two 4 mm length polyethylene tubing (PE-100, 0.86 mm diameter, Clay Adams Co, Parsippany, N.J.) and a 10 inch 3.0 standard silk suture. The silk suture thread is first passed under the aorta in the above mentioned region. The first piece of tubing is then passed over both the ends of the thread to end up resting on the aorta between the celiac and SMA. The silk thread is then looped to leave an unsecured tie. The second piece of tubing is then placed in the loop, perpendicular and on top the first. The silk thread is then tied and the tension on the two ends of the thread increased until there is a 90% reduction of initial aortic blood flow rate as measured on the ultrasonic probe reader. This initial aortic blood flow rate is recorded prior to the placement of the tubings. A 10% baseline blood flow is maintained for of 60 minutes. Rats are kept on a warming blanket throughout the procedure to maintain body temperature of 37° C.

Once the surgery is complete, all rats are given 2 ml of warm saline intraperitoneally to replace insensible and blood volume losses incurred during the surgery. Serum Creatinine levels are measured 24 hours post surgery.

In vivo two-photon microscopy is performed as previously described (Dunn, et al., Am J Physiol Cell Physiol 283: C905-916, 2002; Sutton, et al., Kidney Int 62: 1539-1549, 2002). Sprague-Dawley rats undergo the PAC model and live renal imaging at 24 h is performed using a Bio-Rad MRC-1024 MP Laser Scanning Confocal/Multiphoton scanner (Hercules, Calif.) with an excitation wavelength of 800 nm through a Nikon Diaphot inverted microscope utilizing a 60×NA 1.4 lens. A femoral venous catheter is inserted to gain vascular access for injecting dyes prior to imaging. Assessment of functional renal injury in the form of vascular permeability defects and disruptions in urinary and blood flow is achieved utilizing a nuclear stain (Hoechst-33342, 400 ul, 1.5 mg/ml in 0.9% saline; Molecular Probes, Eugene, Oreg.), a high molecular weight dextran (HMWD) that is not filtered by the glomerulus under normal conditions (500,000 Da, 7.5 mg/ml in 0.9% saline; Molecular Probes, Eugene, Oreg.), and a low molecular weight dextran (LMWD), that is freely filterable (3,000 Da, 20 mg/ml in 0.9% saline; Molecular Probes, Eugene, Oreg.). To differentiate the two dextrans, the HMWD dextran is labeled with fluorescein (Molecular Probes, Eugene, Oreg.) while the LMWD is labeled with Texas Red (Molecular Probes, Eugene, Oreg.). The left kidney of the anesthetized rat is imaged following exteriorization through a retroperitoneal window via a flank incision. Images are analyzed with Metamorph (Universal Imaging, West Chester, Pa.) software. Approximately 10-12 images every 3 min are collected for each animal examined. For studies examining leukocytes in the microvasculature, images obtained are analyzed in a 4×4 grid. Leukocytes are identified by their characteristic to take up the Hoechst nuclear stain. This correlates with the microvasculature and only leukocytes present in the microvasculature itself are counted. Leukocytes in the microvasculature are classified into 3 subtypes namely (i) free flowing—rapid appearance and disappearance during real time imaging in a grid for less than or equal to 2 frames, (ii) static or adherent—attached to microvascular endothelium with no movement, and (iii) rolling—appearance along endothelium surface for 3 or more frames in a grid.

All statistical analyses of plasma samples utilized the two-sample, two-tailed unpaired Student's t-test of significance and linear regression where appropriate. Data are the mean+/−two standard deviations of the mean. Analysis is done using Microsoft Office Excel 8.0 Statistical software as well as EPIINFO v6.0 (CDC, Atlanta, Ga.).

Histopathological analysis is performed on a series of rats 24 hours after PAC. Prior to harvesting, kidneys are perfused briefly through the abdominal aorta with warm phosphate buffered saline (PBS) and subsequently preserved by in vivo perfusion with 4% paraformaldehyde (PFA) solution. Each rat has both kidneys harvested, cut into sagittal slices and immersed in PFA overnight at 4° C. The sections are then embedded in paraffin, and histologic staining with hematoxyline-eosin (H&E) or periodic acid-Schiff (PAS) is done. Histological grading is performed by a renal pathologist (C.L.P.) blinded to the study, for severity of tissue damage as assessed by extent of tubular cell sloughing, loss of proximal tubule brush border, cast formation, tubular dilatation and obstruction. Tubular necrosis scores, as described previously (Jablonski, et al., *Transplantation* 35: 198-204, 1983) for cortical proximal tubule damage and (Kelly, et al., *J Clin Invest* 97: 1056-1063, 1996) for outer medulla tubular damage are also assessed.

As shown in Table 3, the administration of a single subcutaneous dose of human sTM (5 mg/kg) (SEQ ID NO:3) or a sTM variant (SEQ ID NO:10) given 24 hours before PAC ischemic injury produced a significant reduction (P value<0.05) in serum levels of creatinine compared to the saline treated rats. The reduced serum creatinine levels indicate that human sTM and the sTM variant reduced acute renal injury.

TABLE 3

| Treatment | Serum Creatinine (mg/dL) |
| --- | --- |
| saline | 2.27 |
| sTM | 1.31 |
| F376L | 0.85 |

We claim:

1. A soluble thrombomodulin variant consisting of the sequence SEQ ID NO: 10.

2. A pharmaceutical composition comprising the soluble thrombomodulin variant of claim 1.

3. A method of treating acute renal failure comprising administering an effective amount of a soluble thrombomodulin variant that does not activate Protein C to a patient in need thereof wherein the soluble thrombomodulin variant consists of the sequence SEQ ID NO: 10.

4. A method of preventing acute renal failure comprising administering an effective amount of a soluble thrombomodulin variant that does not activate Protein C to a patient in need thereof wherein the soluble thrombomodulin variant consists of the sequence SEQ ID NO: 10.

* * * * *

SEQUENCE LISTING

```
<160> NUMBER OF SEQ ID NOS: 19

<210> SEQ ID NO 1
<211> LENGTH: 575
<212> TYPE: PRT
<213> ORGANISM: Homo sapiens

<400> SEQUENCE: 1

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
```

```
                225                 230                 235                 240
Gly Ala Trp Asp Cys Ser Val Glu Asn Gly Cys Glu His Ala Cys
                245                 250                 255
Asn Ala Ile Pro Gly Ala Pro Arg Cys Gln Cys Pro Ala Gly Ala Ala
                260                 265                 270
Leu Gln Ala Asp Gly Arg Ser Cys Thr Ala Ser Ala Thr Gln Ser Cys
                275                 280                 285
Asn Asp Leu Cys Glu His Phe Cys Val Pro Asn Pro Asp Gln Pro Gly
                290                 295                 300
Ser Tyr Ser Cys Met Cys Glu Thr Gly Tyr Arg Leu Ala Ala Asp Gln
305                 310                 315                 320
His Arg Cys Glu Asp Val Asp Asp Cys Ile Leu Glu Pro Ser Pro Cys
                325                 330                 335
Pro Gln Arg Cys Val Asn Thr Gln Gly Gly Phe Glu Cys His Cys Tyr
                340                 345                 350
Pro Asn Tyr Asp Leu Val Asp Gly Glu Cys Val Glu Pro Val Asp Pro
                355                 360                 365
Cys Phe Arg Ala Asn Cys Glu Tyr Gln Cys Gln Pro Leu Asn Gln Thr
                370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
Cys Asp Pro Asn Thr Gln Ala Ser Cys Glu Cys Pro Glu Gly Tyr Ile
                420                 425                 430
Leu Asp Asp Gly Phe Ile Cys Thr Asp Ile Asp Glu Cys Glu Asn Gly
                435                 440                 445
Gly Phe Cys Ser Gly Val Cys His Asn Leu Pro Gly Thr Phe Glu Cys
                450                 455                 460
Ile Cys Gly Pro Asp Ser Ala Leu Ala Arg His Ile Gly Thr Asp Cys
465                 470                 475                 480
Asp Ser Gly Lys Val Asp Gly Gly Asp Ser Gly Ser Gly Glu Pro Pro
                485                 490                 495
Pro Ser Pro Thr Pro Gly Ser Thr Leu Thr Pro Ala Val Gly Leu
                500                 505                 510
Val His Ser Gly Leu Leu Ile Gly Ile Ser Ile Ala Ser Leu Cys Leu
                515                 520                 525
Val Val Ala Leu Leu Ala Leu Leu Cys His Leu Arg Lys Lys Gln Gly
                530                 535                 540
Ala Ala Arg Ala Lys Met Glu Tyr Lys Cys Ala Ala Pro Ser Lys Glu
545                 550                 555                 560
Val Val Leu Gln His Val Arg Thr Glu Arg Thr Pro Gln Arg Leu
                565                 570                 575

<210> SEQ ID NO 2
<211> LENGTH: 463
<212> TYPE: PRT
<213> ORGANISM: Rattus sp.

<400> SEQUENCE: 2

Lys Leu Gln Pro Lys Gly Ser Gln Cys Val Gly Asn Glu Cys Phe Ala
1               5                   10                  15
Leu Phe Gln Asp Pro Val Thr Phe Leu Asp Ala Ser Gln Ala Cys Gln
                20                  25                  30
Arg Leu Gln Gly His Leu Met Thr Val Arg Ser Ser Val Ala Ala Asp
```

-continued

```
                35                  40                  45
Val Ile Ser Leu Leu Val Ser Asp Ser Met Asp Ser Arg Pro Trp
 50                  55                  60

Ile Gly Leu Gln Leu Pro Gln Gly Cys Gly Asp Pro Val His Leu Gly
 65              70                  75                  80

Pro Leu Arg Gly Phe Gln Trp Val Thr Gly Asp Asn His Thr Ser Tyr
                 85                  90                  95

Ser Arg Trp Ala Arg Pro Asn Asp Gln Ser Pro Leu Cys Gly Pro
                100                 105                 110

Leu Cys Val Thr Val Ser Thr Ala Thr Glu Ala Ala Pro Gly Glu Pro
                115                 120                 125

Ala Trp Glu Glu Lys Pro Cys Glu Asn Glu Thr Lys Gly Phe Leu Cys
130                 135                 140

Glu Phe Tyr Phe Ala Ala Phe Cys Arg Pro Leu Arg Val Asn Thr Arg
145                 150                 155                 160

Asp Pro Glu Gly Ala His Ile Ser Ser Thr Tyr Asn Thr Pro Leu Gly
                165                 170                 175

Val Ser Gly Ala Asp Phe Gln Thr Leu Pro Ile Gly Ser Ser Ala Thr
                180                 185                 190

Val Ala Pro Phe Gly Leu Glu Leu Val Cys Arg Ala Leu Pro Gly Thr
                195                 200                 205

Ser Glu Gly His Trp Thr Arg Glu Val Thr Gly Ala Trp Asn Cys Ser
210                 215                 220

Val Glu Asn Gly Gly Cys Glu Tyr Met Cys Asn Arg Ser Ala Asn Gly
225                 230                 235                 240

Pro Arg Cys Val Cys Pro Ser Gly Asp Leu Gln Ala Asp Gly Arg
                245                 250                 255

Ser Cys Ala Lys Pro Val Ala Gln Leu Cys Asn Glu Leu Cys Gln His
                260                 265                 270

Phe Cys Val Asn Asn Ser Asp Val Pro Gly Ser Tyr Ser Cys Met Cys
                275                 280                 285

Glu Thr Gly Tyr Gln Leu Ala Ala Asp Gly His Arg Cys Glu Asp Val
    290                 295                 300

Asp Asp Cys Lys Gln Gly Pro Asn Pro Cys Pro Gln Leu Cys Ser Asn
305                 310                 315                 320

Thr Glu Gly Gly Phe Glu Cys Arg Cys Tyr Asp Gly Tyr Glu Leu Val
                325                 330                 335

Asp Gly Glu Cys Val Glu Gln Leu Asp Pro Cys Phe Arg Ser Lys Cys
                340                 345                 350

Glu Tyr Gln Cys Gln Pro Val Asn Ser Thr His Tyr Asn Cys Ile Cys
                355                 360                 365

Ala Glu Gly Phe Ala Pro Lys Leu Asp Asp Pro Asp Arg Cys Glu Met
370                 375                 380

Phe Cys Asn Glu Thr Ser Cys Pro Ala Asp Cys Asp Pro Asn Ser Pro
385                 390                 395                 400

Ser Phe Cys Gln Cys Pro Glu Gly Phe Ile Leu Asp Glu Gly Ser Ile
                405                 410                 415

Cys Thr Asp Ile Asp Asn Glu Cys Ser Gln Gly Glu Cys Leu Thr Asn
                420                 425                 430

Glu Cys Arg Asn Leu Pro Gly Ser Tyr Glu Cys Ile Cys Gly Pro Asp
                435                 440                 445

Thr Ala Leu Ala Gly Gln Ile Ser Lys Asp Cys Asp Pro Ile Pro
450                 455                 460
```

-continued

<210> SEQ ID NO 3
<211> LENGTH: 467
<212> TYPE: PRT
<213> ORGANISM: Artificial
<220> FEATURE:
<223> OTHER INFORMATION: Synthetic Construct

<400> SEQUENCE: 3

```
Ala Pro Ala Glu Pro Gln Pro Gly Gly Ser Gln Cys Val His Asp
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Tyr Gln Cys Gln Pro Leu Asn Gln Thr Ser Tyr
        355                 360                 365

Leu Cys Val Cys Ala Glu Gly Phe Ala Pro Ile Pro His Glu Pro His
```

-continued

```
                 370                 375                 380
Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Asn Glu Cys Glu Asn Gly Gly
            420                 425                 430

Phe Cys Ser Gly Val Cys His Asn Leu Pro Gly Thr Phe Glu Cys Ile
        435                 440                 445

Cys Gly Pro Asp Ser Ala Leu Ala Arg His Ile Gly Thr Asp Cys Asp
    450                 455                 460

Ser Gly Lys
465

<210> SEQ ID NO 4
<211> LENGTH: 466
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (358)..(358)
<223> OTHER INFORMATION: Xaa at position 358 is Tyr, Asp, Glu, Asn, or
      Gln
<220> FEATURE:
<221> NAME/KEY: MISC_FEATURE
<222> LOCATION: (376)..(376)
<223> OTHER INFORMATION: Xaa at position 376 is Phe, Gly, Ile, Leu, or
      Val
<220> FEATURE:
<221> NAME/KEY: MISC_FEATURE
<222> LOCATION: (410)..(410)
<223> OTHER INFORMATION: Xaa at position 410 is Pro or Leu

<400> SEQUENCE: 4

Ala Pro Ala Glu Pro Gln Pro Gly Gly Ser Gln Cys Val Glu His Glu
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190
```

```
Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
        210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Xaa Gln Cys Gln Pro Leu Asn Gln Thr Ser Tyr
        355                 360                 365

Leu Cys Val Cys Ala Glu Gly Xaa Ala Pro Ile Pro His Glu Pro His
    370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Xaa Glu Gly Tyr Ile Leu Asp
                405                 410                 415

Asp Gly Phe Ile Cys Thr Asp Ile Asp Glu Cys Glu Asn Gly Gly Phe
            420                 425                 430

Cys Ser Gly Val Cys His Asn Leu Pro Gly Thr Phe Glu Cys Ile Cys
        435                 440                 445

Gly Pro Asp Ser Ala Leu Ala Arg His Ile Gly Thr Asp Cys Asp Ser
    450                 455                 460

Gly Lys
465

<210> SEQ ID NO 5
<211> LENGTH: 467
<212> TYPE: PRT
<213> ORGANISM: Artificial
<220> FEATURE:
<223> OTHER INFORMATION: Synthetic Construct

<400> SEQUENCE: 5

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65              70                  75                  80

Pro Lys Arg Leu Gly Pro Leu Arg Gly Phe Gln Trp Val Thr Gly Asp
```

```
                85                  90                  95
Asn Asn Thr Ser Tyr Ser Arg Trp Ala Arg Leu Asp Leu Asn Gly Ala
                100                 105                 110

Pro Leu Cys Gly Pro Leu Cys Val Ala Val Ser Ala Ala Glu Ala Thr
            115                 120                 125

Val Pro Ser Glu Pro Ile Trp Glu Glu Gln Gln Cys Glu Val Lys Ala
        130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
            195                 200                 205

Pro Pro Gly Ala Val Gln Gly His Trp Ala Arg Glu Ala Pro Gly Ala
        210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Asp Gln Cys Gln Pro Leu Asn Gln Thr Ser Tyr
        355                 360                 365

Leu Cys Val Cys Ala Glu Gly Phe Ala Pro Ile Pro His Glu Pro His
    370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Asn Glu Cys Glu Asn Gly Gly
            420                 425                 430

Phe Cys Ser Gly Val Cys His Asn Leu Pro Gly Thr Phe Glu Cys Ile
        435                 440                 445

Cys Gly Pro Asp Ser Ala Leu Ala Arg His Ile Gly Thr Asp Cys Asp
    450                 455                 460

Ser Gly Lys
465

<210> SEQ ID NO 6
<211> LENGTH: 467
<212> TYPE: PRT
<213> ORGANISM: Artificial
<220> FEATURE:
```

<223> OTHER INFORMATION: Synthetic Construct

<400> SEQUENCE: 6

```
Ala Pro Ala Glu Pro Gln Pro Gly Gly Ser Gln Cys Val Glu His Asp
 1               5                  10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
            35                  40                  45

Ala Ala Asp Val Ile Ser Leu Leu Asn Gly Asp Gly Gly Val Gly
        50                  55                  60

Arg Arg Arg Leu Trp Ile Gly Leu Gln Leu Pro Pro Gly Cys Gly Asp
 65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
                180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
        210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
        290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Glu Gln Cys Gln Pro Leu Asn Gln Thr Ser Tyr
        355                 360                 365

Leu Cys Val Cys Ala Glu Gly Phe Ala Pro Ile Pro His Glu Pro His
    370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
```

```
                              405                 410                 415
Asp Gly Phe Ile Cys Thr Asp Ile Asp Asn Glu Cys Glu Asn Gly Gly
                420                 425                 430

Phe Cys Ser Gly Val Cys His Asn Leu Pro Gly Thr Phe Glu Cys Ile
                435                 440                 445

Cys Gly Pro Asp Ser Ala Leu Ala Arg His Ile Gly Thr Asp Cys Asp
                450                 455                 460

Ser Gly Lys
465

<210> SEQ ID NO 7
<211> LENGTH: 467
<212> TYPE: PRT
<213> ORGANISM: Artificial
<220> FEATURE:
<223> OTHER INFORMATION: Synthetic Construct

<400> SEQUENCE: 7

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
                35                  40                  45

Ala Ala Asp Val Ile Ser Leu Leu Leu Asn Gly Asp Gly Gly Val Gly
            50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
                100                 105                 110

Pro Leu Cys Gly Pro Leu Cys Val Ala Val Ser Ala Ala Glu Ala Thr
                115                 120                 125

Val Pro Ser Glu Pro Ile Trp Glu Glu Gln Gln Cys Glu Val Lys Ala
            130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly Thr
                165                 170                 175

Thr Pro Phe Ala Ala Arg Gly Ala Asp Phe Gln Ala Leu Pro Val Gly
                180                 185                 190

Ser Ser Ala Ala Val Ala Pro Leu Gly Leu Gln Leu Met Cys Thr Ala
                195                 200                 205

Pro Pro Gly Ala Val Gln Gly His Trp Ala Arg Glu Ala Pro Gly Ala
            210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
                260                 265                 270

Leu Cys Glu His Phe Cys Val Pro Asn Pro Asp Gln Pro Gly Ser Tyr
                275                 280                 285

Ser Cys Met Cys Glu Thr Gly Tyr Arg Leu Ala Ala Asp Gln His Arg
                290                 295                 300
```

```
Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Pro Cys Phe
            340                 345                 350

Arg Ala Asn Cys Glu Asn Gln Cys Gln Pro Leu Asn Gln Thr Ser Tyr
                355                 360                 365

Leu Cys Val Cys Ala Glu Gly Phe Ala Pro Ile Pro His Glu Pro His
    370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Asn Glu Cys Glu Asn Gly Gly
            420                 425                 430

Phe Cys Ser Gly Val Cys His Asn Leu Pro Gly Thr Phe Glu Cys Ile
    435                 440                 445

Cys Gly Pro Asp Ser Ala Leu Ala Arg His Ile Gly Thr Asp Cys Asp
450                 455                 460

Ser Gly Lys
465

<210> SEQ ID NO 8
<211> LENGTH: 467
<212> TYPE: PRT
<213> ORGANISM: Artificial
<220> FEATURE:
<223> OTHER INFORMATION: Synthetic Construct

<400> SEQUENCE: 8

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
            35                  40                  45

Ala Ala Asp Val Ile Ser Leu Leu Leu Asn Gly Asp Gly Gly Val Gly
        50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190
```

```
Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Gln Gln Cys Gln Pro Leu Asn Gln Thr Ser Tyr
        355                 360                 365

Leu Cys Val Cys Ala Glu Gly Phe Ala Pro Ile Pro His Glu Pro His
    370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Asn Glu Cys Glu Asn Gly Gly
            420                 425                 430

Phe Cys Ser Gly Val Cys His Asn Leu Pro Gly Thr Phe Glu Cys Ile
        435                 440                 445

Cys Gly Pro Asp Ser Ala Leu Ala Arg His Ile Gly Thr Asp Cys Asp
    450                 455                 460

Ser Gly Lys
465

<210> SEQ ID NO 9
<211> LENGTH: 467
<212> TYPE: PRT
<213> ORGANISM: Artificial
<220> FEATURE:
<223> OTHER INFORMATION: Synthetic Construct

<400> SEQUENCE: 9

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
```

```
                     85                  90                  95
Asn Asn Thr Ser Tyr Ser Arg Trp Ala Arg Leu Asp Leu Asn Gly Ala
                100                 105                 110

Pro Leu Cys Gly Pro Leu Cys Val Ala Val Ser Ala Ala Glu Ala Thr
            115                 120                 125

Val Pro Ser Glu Pro Ile Trp Glu Gln Gln Cys Glu Val Lys Ala
130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
                180                 185                 190

Ser Ser Ala Ala Val Ala Pro Leu Gly Leu Gln Leu Met Cys Thr Ala
            195                 200                 205

Pro Pro Gly Ala Val Gln Gly His Trp Ala Arg Glu Ala Pro Gly Ala
210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
                260                 265                 270

Leu Cys Glu His Phe Cys Val Pro Asn Pro Asp Gln Pro Gly Ser Tyr
            275                 280                 285

Ser Cys Met Cys Glu Thr Gly Tyr Arg Leu Ala Ala Asp Gln His Arg
            290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
                340                 345                 350

Arg Ala Asn Cys Glu Tyr Gln Cys Gln Pro Leu Asn Gln Thr Ser Tyr
            355                 360                 365

Leu Cys Val Cys Ala Glu Gly Ile Ala Pro Ile Pro His Glu Pro His
            370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Asn Glu Cys Glu Asn Gly Gly
                420                 425                 430

Phe Cys Ser Gly Val Cys His Asn Leu Pro Gly Thr Phe Glu Cys Ile
            435                 440                 445

Cys Gly Pro Asp Ser Ala Leu Ala Arg His Ile Gly Thr Asp Cys Asp
450                 455                 460

Ser Gly Lys
465

<210> SEQ ID NO 10
<211> LENGTH: 467
<212> TYPE: PRT
<213> ORGANISM: Artificial
<220> FEATURE:
```

<223> OTHER INFORMATION: Synthetic Construct

<400> SEQUENCE: 10

```
Ala Pro Ala Glu Pro Gln Pro Gly Gly Ser Gln Cys Val Glu His Asp
  1               5                  10                  15

Cys Phe Ala Leu Tyr Pro Gly Pro Ala Thr Phe Leu Asn Ala Ser Gln
             20                  25                  30

Ile Cys Asp Gly Leu Arg Gly His Leu Met Thr Val Arg Ser Ser Val
         35                  40                  45

Ala Ala Asp Val Ile Ser Leu Leu Asn Gly Asp Gly Gly Val Gly
 50                  55                  60

Arg Arg Arg Leu Trp Ile Gly Leu Gln Leu Pro Pro Gly Cys Gly Asp
 65                  70                  75                  80

Pro Lys Arg Leu Gly Pro Leu Arg Gly Phe Gln Trp Val Thr Gly Asp
                 85                  90                  95

Asn Asn Thr Ser Tyr Ser Arg Trp Ala Arg Leu Asp Leu Asn Gly Ala
             100                 105                 110

Pro Leu Cys Gly Pro Leu Cys Val Ala Val Ser Ala Ala Glu Ala Thr
             115                 120                 125

Val Pro Ser Glu Pro Ile Trp Glu Glu Gln Gln Cys Glu Val Lys Ala
         130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                 165                 170                 175

Thr Pro Phe Ala Ala Arg Gly Ala Asp Phe Gln Ala Leu Pro Val Gly
                 180                 185                 190

Ser Ser Ala Ala Val Ala Pro Leu Gly Leu Gln Leu Met Cys Thr Ala
             195                 200                 205

Pro Pro Gly Ala Val Gln Gly His Trp Ala Arg Glu Ala Pro Gly Ala
         210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                 245                 250                 255

Ala Asp Gly Arg Ser Cys Thr Ala Ser Ala Thr Gln Ser Cys Asn Asp
             260                 265                 270

Leu Cys Glu His Phe Cys Val Pro Asn Pro Asp Gln Pro Gly Ser Tyr
         275                 280                 285

Ser Cys Met Cys Glu Thr Gly Tyr Arg Leu Ala Ala Asp Gln His Arg
     290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                 325                 330                 335

Tyr Asp Leu Val Asp Gly Glu Cys Val Glu Pro Val Asp Pro Cys Phe
             340                 345                 350

Arg Ala Asn Cys Glu Tyr Gln Cys Gln Pro Leu Asn Gln Thr Ser Tyr
         355                 360                 365

Leu Cys Val Cys Ala Glu Gly Leu Ala Pro Ile Pro His Glu Pro His
     370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
```

```
                  405                 410                 415
Asp Gly Phe Ile Cys Thr Asp Ile Asp Asn Glu Cys Glu Asn Gly Gly
                420                 425                 430

Phe Cys Ser Gly Val Cys His Asn Leu Pro Gly Thr Phe Glu Cys Ile
                435                 440                 445

Cys Gly Pro Asp Ser Ala Leu Ala Arg His Ile Gly Thr Asp Cys Asp
            450                 455                 460

Ser Gly Lys
465

<210> SEQ ID NO 11
<211> LENGTH: 467
<212> TYPE: PRT
<213> ORGANISM: Artificial
<220> FEATURE:
<223> OTHER INFORMATION: Synthetic Construct

<400> SEQUENCE: 11

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
            35                  40                  45

Ala Ala Asp Val Ile Ser Leu Leu Leu Asn Gly Asp Gly Gly Val Gly
        50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
                100                 105                 110

Pro Leu Cys Gly Pro Leu Cys Val Ala Val Ser Ala Ala Glu Ala Thr
            115                 120                 125

Val Pro Ser Glu Pro Ile Trp Glu Glu Gln Gln Cys Glu Val Lys Ala
        130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly Thr
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300
```

```
Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
            325                 330                 335

Tyr Asp Leu Val Asp Gly Glu Cys Val Glu Pro Val Asp Pro Cys Phe
        340                 345                 350

Arg Ala Asn Cys Glu Tyr Gln Cys Gln Pro Leu Asn Gln Thr Ser Tyr
    355                 360                 365

Leu Cys Val Cys Ala Glu Gly Val Ala Pro Ile Pro His Glu Pro His
370                 375                 380

Arg Cys Gln Met Phe Cys Asn Gln Thr Ala Cys Pro Ala Asp Cys Asp
385                 390                 395                 400

Pro Asn Thr Gln Ala Ser Cys Cys Pro Glu Gly Tyr Ile Leu Asp
                405                 410                 415

Asp Gly Phe Ile Cys Thr Asp Ile Asp Asn Glu Cys Glu Asn Gly Gly
            420                 425                 430

Phe Cys Ser Gly Val Cys His Asn Leu Pro Gly Thr Phe Glu Cys Ile
    435                 440                 445

Cys Gly Pro Asp Ser Ala Leu Ala Arg His Ile Gly Thr Asp Cys Asp
450                 455                 460

Ser Gly Lys
465

<210> SEQ ID NO 12
<211> LENGTH: 467
<212> TYPE: PRT
<213> ORGANISM: Artificial
<220> FEATURE:
<223> OTHER INFORMATION: Synthetic Construct

<400> SEQUENCE: 12

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190
```

```
Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
        210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
        290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Tyr Gln Cys Gln Pro Leu Asn Gln Thr Ser Tyr
        355                 360                 365

Leu Cys Val Cys Ala Glu Gly Ala Pro Ile Pro His Glu Pro His
        370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Asn Glu Cys Glu Asn Gly Gly
            420                 425                 430

Phe Cys Ser Gly Val Cys His Asn Leu Pro Gly Thr Phe Glu Cys Ile
        435                 440                 445

Cys Gly Pro Asp Ser Ala Leu Ala Arg His Ile Gly Thr Asp Cys Asp
        450                 455                 460

Ser Gly Lys
465

<210> SEQ ID NO 13
<211> LENGTH: 467
<212> TYPE: PRT
<213> ORGANISM: Artificial
<220> FEATURE:
<223> OTHER INFORMATION: Synthetic Construct

<400> SEQUENCE: 13

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65              70                  75                  80

Pro Lys Arg Leu Gly Pro Leu Arg Gly Phe Gln Trp Val Thr Gly Asp
```

```
                        85                  90                  95
Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
            115                 120                 125

Val Pro Ser Glu Pro Ile Trp Glu Glu Gln Gln Cys Glu Val Lys Ala
            130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
            165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
            195                 200                 205

Pro Pro Gly Ala Val Gln Gly His Trp Ala Arg Glu Ala Pro Gly Ala
            210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
            245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
            275                 280                 285

Ser Cys Met Cys Glu Thr Gly Tyr Arg Leu Ala Ala Asp Gln His Arg
            290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
            325                 330                 335

Tyr Asp Leu Val Asp Gly Glu Cys Val Glu Pro Val Asp Pro Cys Phe
            340                 345                 350

Arg Ala Asn Cys Glu Tyr Gln Cys Gln Pro Leu Asn Gln Thr Ser Tyr
            355                 360                 365

Leu Cys Val Cys Ala Glu Gly Phe Ala Pro Ile Pro His Glu Pro His
            370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Leu Glu Gly Tyr Ile Leu Asp
            405                 410                 415

Asp Gly Phe Ile Cys Thr Asp Ile Asp Asn Glu Cys Glu Asn Gly Gly
            420                 425                 430

Phe Cys Ser Gly Val Cys His Asn Leu Pro Gly Thr Phe Glu Cys Ile
            435                 440                 445

Cys Gly Pro Asp Ser Ala Leu Ala Arg His Ile Gly Thr Asp Cys Asp
450                 455                 460

Ser Gly Lys
465

<210> SEQ ID NO 14
<211> LENGTH: 463
<212> TYPE: PRT
<213> ORGANISM: Rattus rattus
```

<400> SEQUENCE: 14

```
Lys Leu Gln Pro Lys Gly Ser Gln Cys Val Gly Asn Glu Cys Phe Ala
1               5                   10                  15
Leu Phe Gln Asp Pro Val Thr Phe Leu Asp Ala Ser Gln Ala Cys Gln
            20                  25                  30
Arg Leu Gln Gly His Leu Met Thr Val Arg Ser Ser Val Ala Ala Asp
        35                  40                  45
Val Ile Ser Leu Leu Val Ser Asp Ser Ser Met Asp Ser Arg Pro Trp
50                  55                  60
Ile Gly Leu Gln Leu Pro Gln Gly Cys Gly Asp Pro Val His Leu Gly
65                  70                  75                  80
Pro Leu Arg Gly Phe Gln Trp Val Thr Gly Asp Asn His Thr Ser Tyr
                85                  90                  95
Ser Arg Trp Ala Arg Pro Asn Asp Gln Ser Pro Leu Cys Gly Pro
            100                 105                 110
Leu Cys Val Thr Val Ser Thr Ala Thr Glu Ala Pro Gly Glu Pro
        115                 120                 125
Ala Trp Glu Glu Lys Pro Cys Glu Asn Glu Thr Lys Gly Phe Leu Cys
130                 135                 140
Glu Phe Tyr Phe Ala Ala Phe Cys Arg Pro Leu Arg Val Asn Thr Arg
145                 150                 155                 160
Asp Pro Glu Gly Ala His Ile Ser Ser Thr Tyr Asn Thr Pro Leu Gly
                165                 170                 175
Val Ser Gly Ala Asp Phe Gln Thr Leu Pro Ile Gly Ser Ser Ala Thr
            180                 185                 190
Val Ala Pro Phe Gly Leu Glu Leu Val Cys Arg Ala Leu Pro Gly Thr
        195                 200                 205
Ser Glu Gly His Trp Thr Arg Glu Val Thr Gly Ala Trp Asn Cys Ser
210                 215                 220
Val Glu Asn Gly Gly Cys Glu Tyr Met Cys Asn Arg Ser Ala Asn Gly
225                 230                 235                 240
Pro Arg Cys Val Cys Pro Ser Gly Gly Asp Leu Gln Ala Asp Gly Arg
                245                 250                 255
Ser Cys Ala Lys Pro Val Ala Gln Leu Cys Asn Glu Leu Cys Gln His
            260                 265                 270
Phe Cys Val Asn Asn Ser Asp Val Pro Gly Ser Tyr Ser Cys Met Cys
        275                 280                 285
Glu Thr Gly Tyr Gln Leu Ala Ala Asp Gly His Arg Cys Glu Asp Val
290                 295                 300
Asp Asp Cys Lys Gln Gly Pro Asn Pro Cys Pro Gln Leu Cys Ser Asn
305                 310                 315                 320
Thr Glu Gly Gly Phe Glu Cys Arg Cys Tyr Asp Gly Tyr Glu Leu Val
                325                 330                 335
Asp Gly Glu Cys Val Glu Gln Leu Asp Pro Cys Phe Arg Ser Lys Cys
            340                 345                 350
Glu Tyr Gln Cys Gln Pro Val Asn Ser Thr His Tyr Asn Cys Ile Cys
        355                 360                 365
Ala Glu Gly Phe Ala Pro Lys Leu Asp Asp Pro Asp Arg Cys Glu Met
370                 375                 380
Phe Cys Asn Glu Thr Ser Cys Pro Ala Asp Cys Asp Pro Asn Ser Pro
385                 390                 395                 400
Ser Phe Cys Gln Cys Pro Glu Gly Phe Ile Leu Asp Glu Gly Ser Ile
                405                 410                 415
```

```
Cys Thr Asp Ile Asp Asn Glu Cys Ser Gln Gly Glu Cys Leu Thr Asn
                420                 425                 430
Glu Cys Arg Asn Leu Pro Gly Ser Tyr Glu Cys Ile Cys Gly Pro Asp
            435                 440                 445
Thr Ala Leu Ala Gly Gln Ile Ser Lys Asp Cys Asp Pro Ile Pro
        450                 455                 460

<210> SEQ ID NO 15
<211> LENGTH: 1410
<212> TYPE: DNA
<213> ORGANISM: Artificial
<220> FEATURE:
<223> OTHER INFORMATION: Synthetic Construct

<400> SEQUENCE: 15
gcccctgccg agcctcagcc tggcggcagc cagtgcgtgg agcacgactg cttcgccctg      60
taccccggac cgccaccttt cctgaacgcc agccagatct gcgacggcct gcggggccac     120
ctgatgaccg tgcggagcag cgtggccgcc gacgtgatca gctgctgct gaacggcgac      180 ggcggcgtgg gcaggcggag gctgtggatc ggactgcagc tgccccctgg ctgcggcgac     240
cccaagaggc tgggcccccct gcggggcttc cagtgggtga ccggcgacaa caacaccagc    300
tacagcagat gggccaggct ggacctgaat ggcgcccctc tgtgcggccc actgtgcgtg     360
gccgtgtctg ccgccgaggc caccgtgccc agcgagccca tctgggagga cagcagtgc     420 gaagtgaagg ccgacggctt cctgtgcgag ttccacttcc ccgccacctg caggcctctg    480
gccgtggaac ctggagccgc tgctgccgcc gtgagcatca cctacggcac ccccttcgcc    540
gccagaggcg ccgacttcca ggccctgccc gtgggctctt ctgccgccgt ggcccccctg    600
gggctgcagc tgatgtgcac cgcccctcca ggcgccgtgc agggccactg gccagagaa    660 gcccctggcg cctgggactg cagcgtggag aacggcggct gcgagcacgc ctgcaacgcc    720
atccctggcg cccctaggtg ccagtgccct gccggagccg ccctccaggc cgatggcaga    780
agctgcaccg ccagcgccac ccagagctgc aacgacctgt gcgagcactt ctgcgtgccc    840
aaccccgacc agcccggcag ctacagctgc atgtgcgaga ccggctaccg gctgccgcc     900 gatcagcaca gatgcgagga cgtggacgac tgcatcctgg aacccagccc ctgccccag    960 agatgcgtga cacccagggg cggcttcgag tgccactgct accccaacta cgacctggtg   1020
gacggcgagt gtgtggagcc cgtggacccc tgcttccggg ccaactgcga gtaccagtgc   1080
cagcccctga ccagaccagc tacctgtgcg tgtgcgccg aaggcttcgc ccccatcccc   1140
cacgagcccc accggtgcca gatgttctgc aaccagaccg cctgccctgc cgactgcgac   1200
cccaatcccc aggccagctg cgagtgcccc gagggctaca tcctggacga cggcttcatc   1260
tgcaccgaca tcgacgagtg cgagaatggc ggcttctgca gcggcgtgtg ccacaacctg   1320
cccggcacct tcgagtgcat ctgcggccct gacagcgccc tggccggca tcggcacc    1380 gactgcgata gcggcaagtg atgatctaga                                    1410

<210> SEQ ID NO 16
<211> LENGTH: 1410
<212> TYPE: DNA
<213> ORGANISM: Artificial
<220> FEATURE:
<223> OTHER INFORMATION: Synthetic Construct

<400> SEQUENCE: 16
gcccctgccg agcctcagcc tggcggcagc cagtgcgtgg agcacgactg cttcgccctg      60
taccccggac cgccaccttt cctgaacgcc agccagatct gcgacggcct gcggggccac     120
```

```
ctgatgaccg tgcggagcag cgtggccgcc gacgtgatca gcctgctgct gaacggcgac      180
ggcggcgtgg gcaggcggag gctgtggatc ggactgcagc tgccccctgg ctgcggcgac      240
cccaagaggc tgggccccct gcggggcttc cagtgggtga ccggcgacaa caacaccagc      300
tacagcagat gggccaggct ggacctgaat ggcgcccctc tgtgcggccc actgtgcgtg      360
gccgtgtctg ccgccgaggc caccgtgccc agcgagccca tctgggagga acagcagtgc      420
gaagtgaagg ccgacggctt cctgtgcgag ttccacttcc ccgccacctg caggcctctg      480
gccgtggaac ctggagccgc tgctgccgcc gtgagcatca cctacggcac ccccttcgcc      540
gccagaggcg ccgacttcca ggccctgccc gtgggctctt ctgccgccgt ggcccccctg      600
gggctgcagc tgatgtgcac cgcccctcca ggcgccgtgc agggccactg gccagagaa       660
gcccctggcg cctgggactg cagcgtggag aacggcggct gcgagcacgc ctgcaacgcc      720
atccctggcg cccctaggtg ccagtgccct gccggagccg ccctccaggc cgatggcaga      780
agctgcaccg ccagcgccac ccagagctgc aacgacctgt gcgagcactt ctgcgtgccc      840
aaccccgacc agcccggcag ctacagctgc atgtgcgaga ccggctaccg gctggccgcc      900
gatcagcaca gatgcgagga cgtggacgac tgcatcctgg aacccagccc tgcccccag      960
agatgcgtga cacccagggg cggcttcgag tgccactgct accccaacta cgacctggtg     1020
gacggcgagt gtgtggagcc cgtggacccc tgcttccggg ccaactgcga ggagcagtgc     1080
cagcccctga accagaccag ctacctgtgc gtgtgcgccg aaggcttcgc ccccatcccc     1140
cacgagcccc accggtgcca gatgttctgc aaccagaccg cctgccctgc cgactgcgac     1200
cccaataccc aggccagctg cgagtgcccc gagggctaca tcctggacga cggcttcatc     1260
tgcaccgaca tcgacgagtg cgagaatggc ggcttctgca gcggcgtgtg ccacaacctg     1320
cccggcacct tcgagtgcat ctgcggccct gacagcgccc tggcccggca catcggcacc     1380
gactgcgata cggcaagtg atgatctaga                                       1410
```

<210> SEQ ID NO 17
<211> LENGTH: 1410
<212> TYPE: DNA
<213> ORGANISM: Artificial
<220> FEATURE:
<223> OTHER INFORMATION: Synthetic Construct

<400> SEQUENCE: 17

```
gcccctgccg agcctcagcc tggcggcagc cagtgcgtgg agcacgactg cttcgccctg       60
taccccggac ccgccacctt cctgaacgcc agccagatct gcgacggcct gcggggccac      120
ctgatgaccg tgcggagcag cgtggccgcc gacgtgatca gcctgctgct gaacggcgac      180
ggcggcgtgg gcaggcggag gctgtggatc ggactgcagc tgccccctgg ctgcggcgac      240
cccaagaggc tgggccccct gcggggcttc cagtgggtga ccggcgacaa caacaccagc      300
tacagcagat gggccaggct ggacctgaat ggcgcccctc tgtgcggccc actgtgcgtg      360
gccgtgtctg ccgccgaggc caccgtgccc agcgagccca tctgggagga acagcagtgc      420
gaagtgaagg ccgacggctt cctgtgcgag ttccacttcc ccgccacctg caggcctctg      480
gccgtggaac ctggagccgc tgctgccgcc gtgagcatca cctacggcac ccccttcgcc      540
gccagaggcg ccgacttcca ggccctgccc gtgggctctt ctgccgccgt ggcccccctg      600
gggctgcagc tgatgtgcac cgcccctcca ggcgccgtgc agggccactg gccagagaa       660
gcccctggcg cctgggactg cagcgtggag aacggcggct gcgagcacgc ctgcaacgcc      720
atccctggcg cccctaggtg ccagtgccct gccggagccg ccctccaggc cgatggcaga      780
```

```
agctgcaccg ccagcgccac ccagagctgc aacgacctgt gcgagcactt ctgcgtgccc      840
aaccccgacc agcccggcag ctacagctgc atgtgcgaga ccggctaccg gctggccgcc      900
gatcagcaca gatgcgagga cgtggacgac tgcatcctgg aacccagccc ctgccccag       960 agatgcgtga acacccaggg cggcttcgag tgccactgct accccaacta cgacctggtg     1020
gacggcgagt gtgtggagcc cgtggacccc tgcttccggg ccaactgcga gtaccagtgc     1080
cagcccctga accagaccag ctacctgtgc gtgtgcgccg aaggcatcgc ccccatcccc     1140
cacgagcccc accggtgcca gatgttctgc aaccagaccg cctgccctgc cgactgcgac     1200
cccaataccc aggccagctg cgagtgcccc gagggctaca tcctggacga cggcttcatc     1260
tgcaccgaca tcgacgagtg cgagaatggc ggcttctgca gcggcgtgtg ccacaacctg     1320
cccggcacct tcgagtgcat ctgcggccct gacagcgccc tggcccggca catcggcacc     1380
gactgcgata gcggcaagtg atgatctaga                                      1410
```

<210> SEQ ID NO 18
<211> LENGTH: 1410
<212> TYPE: DNA
<213> ORGANISM: Artificial
<220> FEATURE:
<223> OTHER INFORMATION: Synthetic Construct

<400> SEQUENCE: 18

```
gcccctgccg agcctcagcc tggcggcagc cagtgcgtgg agcacgactg cttcgccctg       60
taccccggac ccgccacctt cctgaacgcc agccagatct cgacggcct gcggggccac       120 ctgatgaccg tgcggagcag cgtggccgcc gacgtgatca gcctgctgct gaacggcgac      180
ggcggcgtgg gcaggcggag gctgtggatc ggactgcagc tgccccctgg ctgcggcgac      240
cccaagaggc tgggccccct gcggggcttc cagtgggtga ccggcgacaa caacaccagc      300
tacagcagat gggccaggct ggacctgaat ggcgccccctc tgtgcggccc actgtgcgtg      360
gccgtgtctg ccgccgaggc caccgtgccc agcgagccca tctgggagga acagcagtgc      420
gaagtgaagg ccgacggctt cctgtgcgag ttccacttcc ccgccacctg caggcctctg      480
gccgtggaac ctggagccgc tgctgccgcc gtgagcatca cctacggcac ccccttcgcc      540
gccagaggcg ccgacttcca ggccctgccc gtgggctctt ctgccgccgt ggccccctg       600 gggctgcagc tgatgtgcac cgccctcca ggcgccgtgc agggccactg gccagagaa       660 gcccctggcg cctgggactg cagcgtggag aacggcggct gcgagcacgc ctgcaacgcc      720
atccctggcg cccctaggtg ccagtgccct gccggagccg ccctccaggc cgatggcaga      780
agctgcaccg ccagcgccac ccagagctgc aacgacctgt gcgagcactt ctgcgtgccc      840
aaccccgacc agcccggcag ctacagctgc atgtgcgaga ccggctaccg gctggccgcc      900
gatcagcaca gatgcgagga cgtggacgac tgcatcctgg aacccagccc ctgccccag       960 agatgcgtga acacccaggg cggcttcgag tgccactgct accccaacta cgacctggtg     1020
gacggcgagt gtgtggagcc cgtggacccc tgcttccggg ccaactgcga gtaccagtgc     1080
cagcccctga accagaccag ctacctgtgc gtgtgcgccg aaggcctggc ccccatcccc     1140
cacgagcccc accggtgcca gatgttctgc aaccagaccg cctgccctgc cgactgcgac     1200
cccaataccc aggccagctg cgagtgcccc gagggctaca tcctggacga cggcttcatc     1260
tgcaccgaca tcgacgagtg cgagaatggc ggcttctgca gcggcgtgtg ccacaacctg     1320
cccggcacct tcgagtgcat ctgcggccct gacagcgccc tggcccggca catcggcacc     1380
gactgcgata gcggcaagtg atgatctaga                                      1410
```

<210> SEQ ID NO 19
<211> LENGTH: 1410
<212> TYPE: DNA
<213> ORGANISM: Artificial
<220> FEATURE:
<223> OTHER INFORMATION: Synthetic Construct

<400> SEQUENCE: 19

```
gcccctgccg agcctcagcc tggcggcagc cagtgcgtgg agcacgactg cttcgccctg       60
taccccggac ccgccacctt cctgaacgcc agccagatct gcgacggcct gcggggccac      120
ctgatgaccg tgcggagcag cgtggccgcc gacgtgatca gcctgctgct gaacggcgac      180
ggcggcgtgg gcaggcggag gctgtggatc ggactgcagc tgcccectgg ctgcggcgac      240
cccaagaggc tgggcccect gcggggcttc cagtgggtga ccggcgacaa caacaccagc      300
tacagcagat gggccaggct ggacctgaat ggcgccctc tgtgcggccc actgtgcgtg      360
gccgtgtctg ccgccgaggc caccgtgccc agcgagccca tctgggagga acagcagtgc      420
gaagtgaagg ccgacggctt cctgtgcgag ttccacttcc ccgccacctg caggcctctg      480
gccgtggaac ctggagccgc tgctgccgcc gtgagcatca cctacggcac ccccttcgcc      540
gccagaggcg ccgacttcca ggccctgccc gtgggctctt ctgccgccgt ggccccctg      600
gggctgcagc tgatgtgcac cgcccctcca ggcgccgtgc agggccactg gccagagaa      660
gccectggcg cctgggactg cagcgtggag aacggcggct gcgagcacgc ctgcaacgcc      720
atccctggcg cccctaggtg ccagtgccct gccggagccg ccctccaggc cgatggcaga      780
agctgcaccg ccagcgccac ccagagctgc aacgacctgt gcgagcactt ctgcgtgccc      840
aaccccgacc agcccggcag ctacagctgc atgtgcgaga ccggctaccg gctggccgcc      900
gatcagcaca gatgcgagga cgtggacgac tgcatcctgg aacccagccc ctgcccccag      960
agatgcgtga cacccaggg cggcttcgag tgccactgct accccaacta cgacctggtg     1020
gacggcgagt gtgtggagcc cgtggacccc tgcttccggg ccaactgcga gtaccagtgc     1080
cagcccctga accagaccag ctacctgtgc gtgtgcgccg aaggcttcgc ccccatcccc     1140
cacgagcccc accggtgcca gatgttctgc aaccagaccg cctgccctgc cgactgcgac     1200
cccaataccc aggccagctg cgagtgcctg gagggctaca tcctggacga cggcttcatc     1260
tgcaccgaca tcgacgagtg cgagaatggc ggcttctgca gcggcgtgtg ccacaacctg     1320
cccggcacct tcgagtgcat ctgcggccct gacagcgccc tggcccggca catcggcacc     1380
gactgcgata gcggcaagtg atgatctaga                                      1410
```